Figure 1:
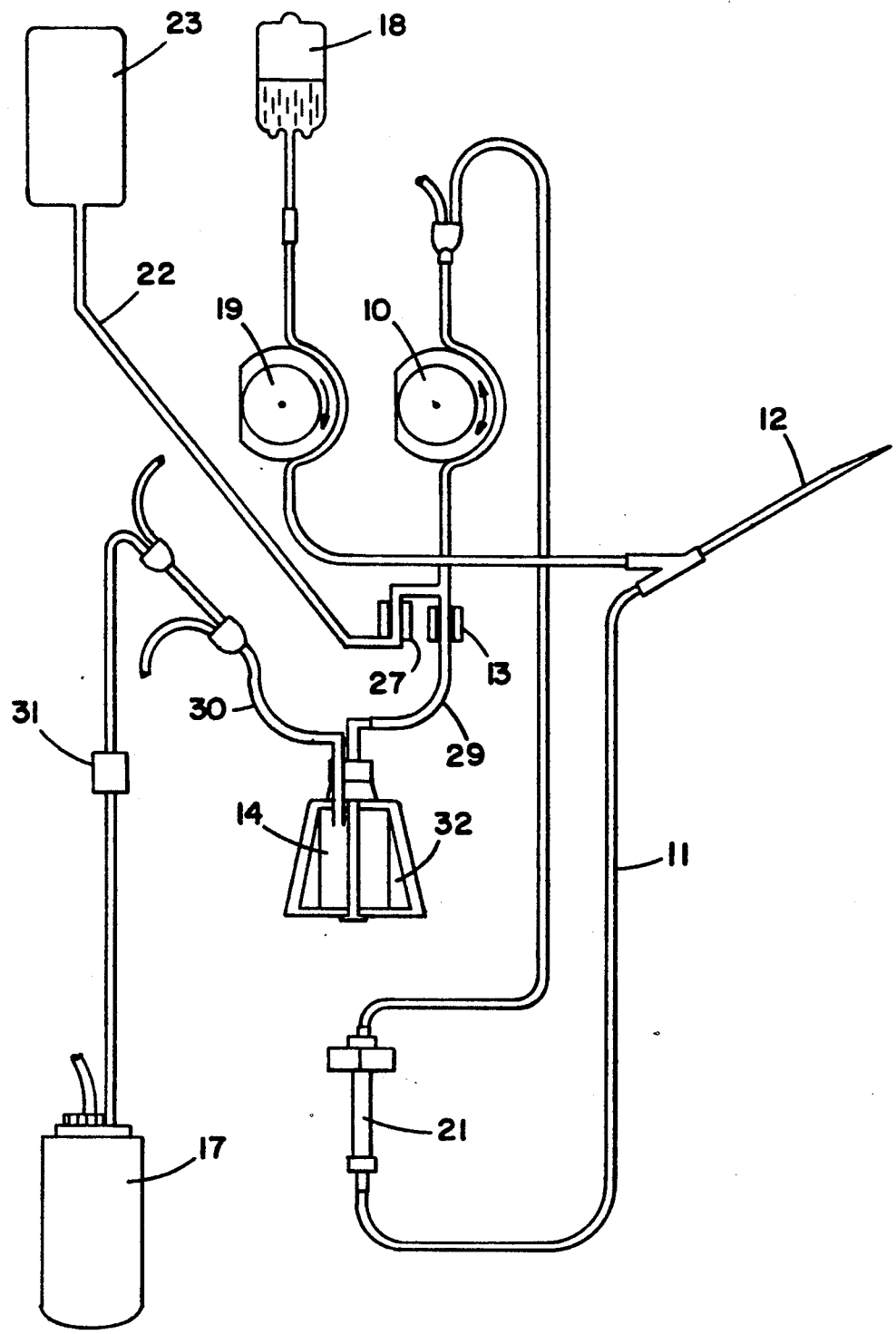

United States Patent [19]

Jonsson

[11] Patent Number: 5,147,290
[45] Date of Patent: Sep. 15, 1992

[54] METHOD AND MACHINE BASED ON THE PRINCIPLE OF CENTRIFUGATION FOR CYTAPHERESIS SUCH AS PLATELET APHERESIS, AND FOR PLASMA EXCHANGE TREATMENT

[75] Inventor: Svante U. R. Jonsson, Glumslöv, Sweden

[73] Assignee: Stafilum AB, Uppsala, Sweden

[21] Appl. No.: 633,082

[22] Filed: Dec. 21, 1990

Related U.S. Application Data

[63] Continuation of Ser. No. 265,138, filed as PCT/SE87/00213, Apr. 24, 1987, abandoned.

[30] Foreign Application Priority Data

Apr. 24, 1986 [SE] Sweden ................. 8601891

[51] Int. Cl.⁵ ............................................. A61M 37/00
[52] U.S. Cl. ........................................... 604/5; 604/6; 494/27
[58] Field of Search ............................ 604/4–6; 494/1, 23, 27, 29, 35, 37

[56] References Cited

U.S. PATENT DOCUMENTS

| Re. 31,688 | 9/1984 | Popovich et al. . | |
|---|---|---|---|
| 3,482,575 | 12/1969 | Glaff et al. . | |
| 4,086,924 | 5/1978 | Latham, Jr. . | |
| 4,185,629 | 1/1980 | Cullis et al. . | |
| 4,285,464 | 8/1981 | Latham, Jr. | 604/6 |
| 4,303,193 | 12/1981 | Latham, Jr. | 604/6 |
| 4,464,167 | 8/1984 | Schoendorfer et al. | 604/6 |
| 4,648,866 | 3/1987 | Malbrancq et al. . | |
| 4,655,742 | 4/1987 | Vantard . | |
| 4,657,529 | 4/1987 | Prince et al. . | |
| 4,687,580 | 8/1987 | Malbrancq et al. | 604/6 |

FOREIGN PATENT DOCUMENTS

| 0171749 | 7/1985 | European Pat. Off. . |
|---|---|---|
| WO86/00231 | 1/1986 | PCT Int'l Appl. . |
| WO86/01426 | 3/1986 | PCT Int'l Appl. . |

OTHER PUBLICATIONS

Figure 9G Making Platelet Cut Haemonetics, Extended Storage Platelet ESP Pack (1981).

Primary Examiner—Stephen C. Pellegrino
Assistant Examiner—Michael Rafa
Attorney, Agent, or Firm—Merchant, Gould, Smith, Edell, Welter & Schmidt

[57] ABSTRACT

Machine for cytapheresis such as platelet apheresis, and for plasma exchange treatment having control means (13, 27) for admixture of a liquid to flow of blood passing through a connection (29) between a pump (10) and a separating means (14) for separation of blood by centrifugation into various components. The invention also relates to a method in operating such a machine, and a method for cytapheresis such as platelet apheresis, wherein said liquid is admixed to blood being drawn from a donor/patient and/or being returned from the separation process to the donor/patient.

16 Claims, 2 Drawing Sheets

METHOD AND MACHINE BASED ON THE PRINCIPLE OF CENTRIFUGATION FOR CYTAPHERESIS SUCH AS PLATELET APHERESIS, AND FOR PLASMA EXCHANGE TREATMENT

This application is a continuation of Ser. No. 07/265,138 filed as PCT/SE87/00213, Apr. 24, 1987, now abandoned.

The invention concerns methods and machine for cytapheresis such as platelet apheresis, and for plasma exchange treatment.

For plasma exchange treatment of a patient, whereby plasma is separated from the patient's blood (because the plasma may lack a certain substance or alternatively may contain substance(s) that cause(s) disease or may be generated by the disease and in turn give rise to significant troubles) and substitution fluid is added to the patient's blood, until now one has been forced to use machinery requiring two separate blood vessel connections through intravenous needles, catheters or the like, one connection for blood flow out from the patient and the other for the return flow back to the patient. This holds true irrespective of the principle applied for separation of blood, centrifugation or filtration. Dual connection has been the only feasible arrangement when running continuous blood separation procedures by using equipment without reservoir functions.

As an early example of the principle of construction and operation of machinery with reservoir function one should mention equipment available from the early 1970's (first made by Haemonetics Corporation, 400 Wood Road, Braintree, Mass. 02184, U.S.A.), by which blood is drawn from the patient to the equipment through one of the two blood lines connecting with the patient in order to obtain separation of the components of blood by centrifugation in a rotating rigid container (Latham bowl), usually with an effective volume of approximately 225 ml. During this part of the procedure the container is being filled by "packed" blood cells as first the air and then the bulk of the blood plasma, which simultaneously has been separated from the cells, leave the container. Using such a construction it repeatedly becomes necessary—at intervals of several minutes—to interrupt the blood flow from the patient and stop the rotor of the centrifugal device in order to make possible the retransfusion of blood cells to the patient. Earlier, this retransfusion has been preceeded by emptying the blood cells from the previously rotating container to another interspaced container (a capacity vessel, in practice an initially empty blood transfusion plastic bag) in order to infuse them to the patient by conventional "drip" technique, exploiting gravity alternatively by using a separate pump, in both cases usually through the second blood vessel connection, starting simultaneously with a new cycle of drawing blood from the patient.

However, during the 1980's Haemonetics Inc. by their models of the V50-series have automated retransfusion with satisfactory control to the effect that the apheresis donor/patient is protected against infusion of blood with too high a pressure and against inadvertent administration of air. Exploiting the reservoir function for packed blood cells available in the Latham bowl as used in a blood separator such as Haemonetics V50-1, cytapheresis (including platelet apheresis or thromb[ocyt]apheresis, leuk[ocyt]apheresis and lymph[ocyt]apheresis) may routinely be performed as a single-needle technique. Thus, drawing blood from the donor/patient as well as retransfusion may be carried out through one and the same connection, as a rule by means of an intravenous syringe in the antecubital fold. Administration of the plasma (or substitution fluid), needed during any lengthy treatment, is then likewise carried out by allowing the intended volume of such fluid to pass or be drawn by suction through and into the top of the bowl, previously rotating but now standing still, while the bowl is being emptied from the bottom. The drawbacks of this design are manifest by the return flow speed being limited, partly because the high viscosity of (the first fraction of retransfused) packed red cells causes increased friction of flow and consequently increased internal pressure in the tubing and the receiving blood vessel, and partly because of the limited capacity of donors/patients to metabolize the calcium ionbinding citrate (admixed inter alia as an inhibitor to coagulation), present in the plasma given (back) to the donor/patient (in exchange). A significant drawback is then the long time required for retransfusion.

The primary purpose of the invention is to produce improved technical possibilities for more rapid cytapheresis procedures, plasma exchange treatment and plasma donation, respectively, by utilizing only one blood vessel connection while eliminating the drawbacks of presently existing equipment separating blood by centrifugation.

For the attainment of this purpose the invention provides a machine for cytapheresis such as platelet apheresis, and for plasma exchange treatment and plasma donation, comprising a donor tubing to be connected to a donor patient for drawing blood therefrom and subsequently returning blood thereto, separating means for separation of blood by centrifugation into various components of which plasma is one, having a reservoir for blood cells, a pump capable of operating in two opposite directions, a first connection between said pump and said donor tubing, a second connection between said pump and said separating means, a container for liquid, a third connection from said container to said second connection, and control means for admixture of liquid from said container through said third connection to flow of blood passing through said second connection.

In addition to the fact that such a machine through one donor/patient connection may alternate between drawing blood from the donor and retransfusing concentrated blood with reduced plasma content and admix plasma from that same donor plasma back to him/her through one and the same tubing, i.a. in addition to the treatment being simplified for the donor/patient and the personnel involved as compared to two-needle procedures. When concentrated blood is given back to the donor/patient, in fact already by a small addition of saline solution (10-20 percent) it may be diluted to the effect that the blood cells easier and quicker may pass into and through narrow tubing and blood vessels. Inversely, dilution of citrated plasma by simultaneous administration of packed blood cells makes the stress of a given amount of citrated plasma, which should be returned during each cycle, more tolerable, since that plasma volume is given back during a longer period of time without the treatment requiring longer overall time. Moreover, the increased retransfusion speed obtainable by mixing the two flows, according to my experience usually up to 130 ml per minute, causes the needle and/or catheter being part of the connection to the patient's blood vessel to be repeatedly flushed at high speed before each new draw phase. According to my experience, in this way one enjoys elimination or significant reduction of tendencies to obliteration of the donor/patient connecting blood line, in particular of the needle, a problem often appearing with lower standard speeds of drawing and returning blood. Furthermore, if the needle/catheter is positioned in the blood vessel so that passage is narrow, it is usually much facilitated by dilution. Thus, increased counter-pressure is avoided during retransfusion (particularly of the packed cells) through narrow passages and vessels as well as the related drawbacks.

The invention also provides a method in operating a machine for cytapheresis such as platelet apheresis, and for plasma exchange treatment, comprising a donor tubing to be connected to a donor/patient for drawing of blood therefrom and subsequently returning blood thereto, separating means for separation of blood by centrifugation into various components of which plasma is one, having a reservoir for blood cells, a pump capable of operating in two opposite directions, a first connection between said pump and said donor tubing, a second connection between said pump and said separating means, a container for liquid, a third connection from said container to said second connection, wherein liquid from said container is admixed through said third connection to flow of blood passing through said second connection.

Moreover the invention provides a method for cytapheresis such as platelet apheresis, and for plasma exchange treatment, comprising the steps of drawing blood from a donor/patient, separating by centrifugation the blood into various components of which plasma is one, returning blood from the separation step to the donor/patient, and admixing a liquid to blood being returned to the donor/patient, as well as a method for cytapheresis such as platelet apheresis, comprising the steps of drawing blood from a donor/patient, admixing plasma to said blood being drawn, separating by centrifugation the blood admixed with said plasma into various components of which plasma is one, said separated plasma being used as the plasma admixed to the blood being drawn, and returning blood from the separation step to the donor/patient.

Figure 2:
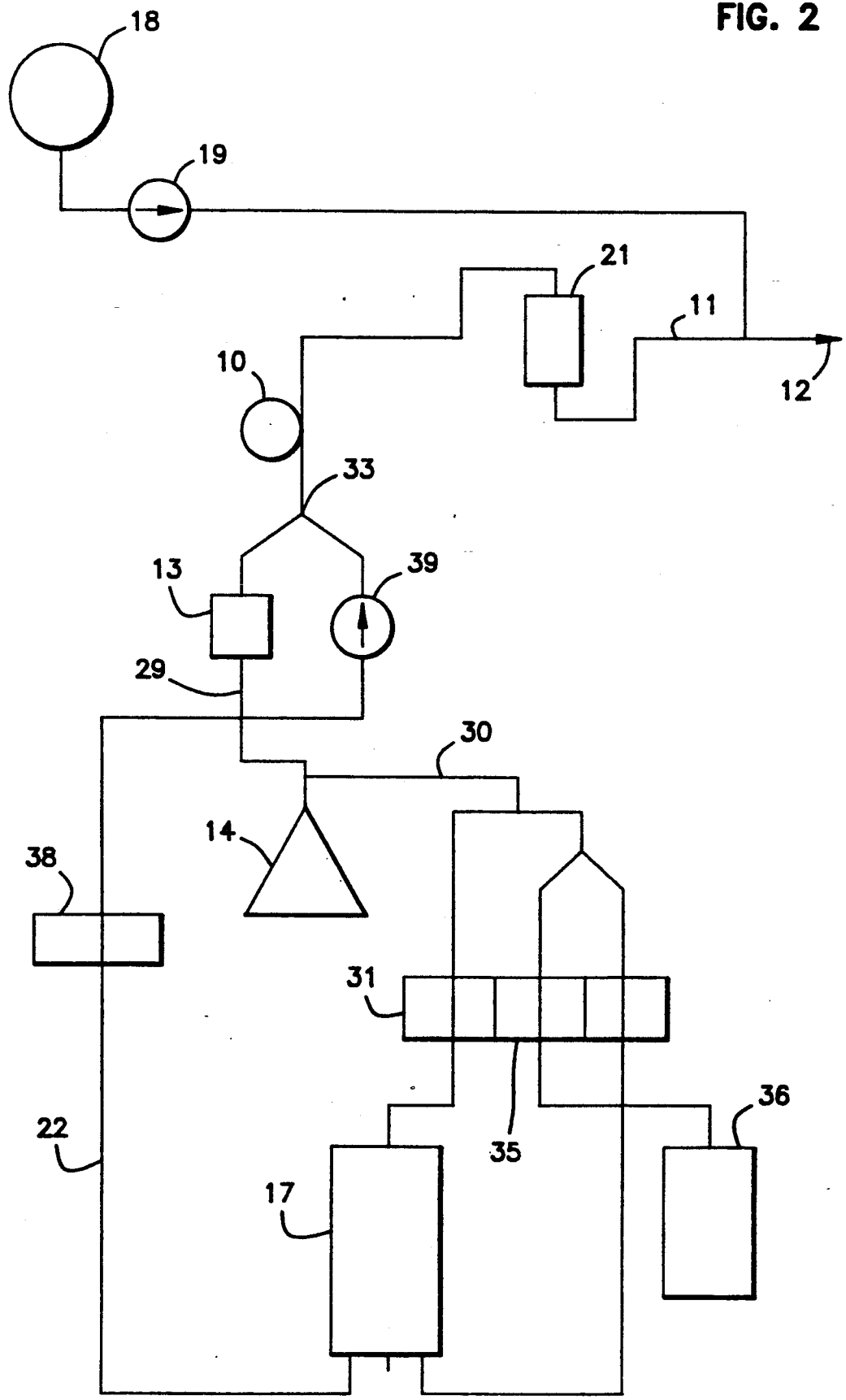

For a more detailed explanation of the invention reference is made to the accompanying diagrammatic drawings, wherein FIG. 1 discloses an embodiment of the machine according to the invention for cytapheresis and for plasma exchange treatment of patients; and FIG. 2 discloses another embodiment of the machine.

In certain automated machines (e.g. as made by Haemonetics) for specialized blood donations (cytapheresis such as platelet apheresis, plasma donation, etc) or for patient treatment the separation means is a rotatable container (e.g. a Latham bowl) with two tubing connections, one for the flow of blood to the bowl and, in the return mode for the flow of concentrated cells therefrom and the other for deaeration, discharge of plasma, platelets etc and, in the return mode, for delivering plasma, other substitution fluids, and air (back) to the top of the bowl. According to the invention the admixture of substitution fluid to the blood returned to the donor/patient is achieved by arranging for valves to open and close alternately with each other. The embodiment of FIG. 1 is according to this scheme.

In FIG. 1 the separating means is of the type referred to above and thus in the shape of a rotatable container (Latham bowl) and is designated 14. A pump 10 is at one side thereof via a valve 13 connected to a tubing 29 for the flow of blood to and from the rotatable container 14, while a connection 30 of the container for deaeration and discharge of plasma etc is connected with a plasma recipient 17 for the collection of plasma and air via a valve 31. A tubing 22, which is connected to a reservoir 23 for substitution fluid via a valve 27, extends to said one side of the pump 10 and is connected to the tubing between the pump and the valve 13. A mixing container 21, which may be designed as a drip chamber, is integrated into a tubing 11 between the other side of the pump 10 and a needle 12 and serves at advantage not only as a mixing chamber but also as a bubble trap. A reservoir 18 for anticoagulant solution is connected to the needle 12 via a pump 19.

The embodiment disclosed in FIG. 1 is operated as follows: When drawing blood from the donor/patient the pump 10 is operating in such a direction that it has its sucking side connected to the donor/patient tubing 11 and its pressure side connected to the rotatable container 14. When blood is drawn according to FIG. 1, the valve 13 is open and the valve 27 is closed, while the valve 31 is open so that the tubing 30 is connected with the plasma recipient 17. The pump 10 draws blood from the donor/patient while anticoagulant solution is proportionally admixed to the blood from the reservoir 18 by means of the pump 19. Blood is supplied to the rotating rotatable container 14, in which blood cells accumulate towards the periphery, as is indicated at 32, while air and then plasma are discharged to the plasma recipient 17.

Drawing blood from the donor/patient usually continues until the rotating rotatable container 14 is nearly filled with blood cells, the corresponding plasma having been discharged. Several possibilities exist such as harvesting platelets, leukocytes or lymphocytes by applying different techniques, one category of which comprises the supply of donor plasma from the plasma recipient through a separate tubing to the bowl at increasing speed such as to elutriate first platelets of relatively low specific gravity carried away with the centripetal flow of plasma through the still rotating rotatable container 14, in which the centrifugal force is still set to be sufficient to keep the bulk of blood cells from being discharged also (so called surge procedure established and patented by Haemonetics Corporation).

During retransfusion the direction of rotation of the pump 10 is reversed and the pump 19 is standing still. The rotatable container 14, too, is standing still, and blood is now being sucked from the bottom of the reservoir at the same time as air is sucked into the top of the reservoir. During retransfusion the valves 13 and 27 open and close alternately in relation to each other for the purpose of dilution of the blood to be retransfused with plasma (substitution fluid). As a consequence of the periodic change of positions of the valves 13 and 27, the mixing container 21 will receive, in an alternating fashion, concentrated blood cells and plasma (substitution fluid) for administration to the patient through the donor/patient tubing 11 and needle 12 along with the blood, now with much reduced viscosity after dilution. The periods of keeping the valve 13 open and the valve 27 closed and vice versa, respectively, need not be the same. Rather it is readily possible with computer technology to monitor these periods of time so as to control the degree of dilution by blood according to the intentions in the case at hand, e.g. in order to arrange for the plasma collected during drawing from a cytapheresis donor to be given back, the plasma recipient 17 being emptied at the same time as the rotatable container 14 for the concentrated blood cells before the start of the following draw cycle.

In FIG. 2 the separation means is also of the type referred to above, including a rotatable container (Latham bowl) designated 14. The pump 10 is at one side thereof connected to the tubing 29 for the supply and discharge of blood to respectively from the container 14, while the connection 30 thereof for deaeration and discharge of plasma and platelets via the valve 31 is connected with the plasma recipient 17 and via a valve 35 with a container (bag) 36 for platelets.

In this embodiment an additional pump 39 is arranged for, which at its sucking side via a valve 38 is connected via the tubing 22 to the plasma recipient 17, and at its pressure side is connected to the tubing 11 between the pump 10 and the rotatable container 14 via a tubing branching 33 and a valve 13. The other side of the pump 10 is connected by way of the dripping chamber 21 to the tubing 11, which in turn is connected with the intravenous needle 12. Supply of anticoagulant close to the needle 12 is arranged by means of the container 18 and the pump 19 in the manner discribed above.

During the draw phase the pump 10 is drawing blood while anticoagulant citrate is proportionally administered to the blood and citrated blood is supplied to the rotatable container 14, rotating at more than 4,000 r.p.m., in which the blood cells accumulate along the periphery, while air and plasma are discharged to the plasma recipient 17, the valve 31 being open and the valve 35 closed. During the draw phase, as soon as plasma is present in container 17, through the action of pump 39 a flow of plasma is added to the flow of blood from the donor/patient for the purpose of increasing the yield of platelets, particularly from donors/patients that bleed slowly. Because of the closed circuit of flow, the flow of plasma from the rotating rotatable bowl to the container will increase correspondingly. Also, it is possible to leave a suitable amount of plasma in the container from a previous draw plus return cycle so as to make possible earlier addition of a flow of plasma to blood being drawn from the donor/patient. Platelets (platelet rich plasma) may be collected in the container 36, the valve 31 then being closed and valve 35 being open as platelets are discharged from the rotating container, e.g. during the so called surge procedure, established and patented by Haemonetics Corporation. Typically, addition of a flow of plasma of about 20 to 60 ml per minute to a flow of blood of 80 down to 40 ml per minute (so that total flow will not surpass 100-110 ml per minute) causes an increase of platelet yield of 20-30 (−40) per cent over the yield from standard procedure.

During retransfusion the direction of rotation of the pump 10 is reversed, and the pump 19 is inoperative. The rotatable container 14 is also standing still, and blood will now be sucked from the container at the same time as air is being sucked into the container. During retransfusion the red cell concentrate to be given back is diluted with plasma from the container 17, being supplied to the tubing branch 33 via the valve 38 by means of the pump 39. By means of the the two pumps the flow of plasma back to a platelet donor may be controlled, the plasma being well mixed with red cells from the rotatable container 14. The speed of pump 39 then ought to be controlled between a speed, which is substantially the same as the speed of pump 10, and a speed which is significantly greater than the speed of pump 10. In this way an improved, shorter return cycle is achieved.

I claim:

1. Machine for platelet apheresis comprising:
   (-) a tubing operable for connection to a donor/patient for the drawing of blood therefrom and subsequent return of platelet depleted blood thereto;
   (-) a centrifugal separating means for separation of blood into various components including at least a cell enriched fraction, a platelet enriched fraction, and a plasma fraction;
   (-) a reservoir for the cell enriched fraction which forms an integral portion of the centrifugal separating means;
   (-) a first pump capable of operating in two opposite directions;
   (-) a first connection between said first pump and said tubing;
   (-) a second connection between said first pump and said separating means;
   (-) a first container for said plasma fraction;
   (-) a third connection from said first container to said separating means;
   (-) a second container for said platelet enriched fraction;
   (-) a fourth connection from said second container to said separating means;
   (-) a fifth connection from said first container to said second connection whereby a junction of said fifth connection and said second connection is formed; and
   (-) control means operable during return of platelet depleted blood to the donor/patient for admixture of said plasma fraction from said first container through said fifth connection to flow of said cell enriched fraction from said reservoir passing through said second connection.

2. Machine as in claim 1, wherein said control means comprises means for opening and closing alternately and repetitively (i) said second connection between said centrifugal separation means and said junction of said second connection and said fifth connection, and (ii) said fifth connection, respectively.

3. Machine as in claim 1, wherein said control means comprises a second pump for driving a flow of said plasma fraction through said fifth connection, and means controlling operation of said second pump.

4. Method for effecting platelet apheresis comprising the steps of:
   (-) connecting a donor/patient to a machine which comprises: (*) a donor tubing operable for connection to a donor/patient for the drawing of blood therefrom and subsequent return of platelet depleted blood thereto; (*) a centrifugal separating means for separation of blood into various components including at least a cell enriched fraction, a platelet enriched fraction, and a plasma fraction; (*) a reservoir for the cell enriched fraction which forms an integral portion of the centrifugal separating means; (*) a first pump capable of operating in two opposite directions; (*) a first connection between said first pump and said donor tubing; (*) a second connection between said first pump and said separating means; (*) a first container for said plasma fraction; (*) a third connection from said first container to said separating means; (*) a second container for said platelet enriched fraction; (*) a fourth connection from said second container to said separating means; (*) a fifth connection from said first container to said second connection whereby a junction of said fifth connection and said second connection is formed; and (*) control means operable during return of platelet depleted blood to the donor/patient for admixture of said plasma fraction from said first container through said fifth connection to flow of said cell enriched fraction from said reservoir passing through said second connection (-) withdrawing blood from said donor/patient into said machine;

(-) separating said withdrawn blood into at least a cell enriched fraction, a platelet enriched fraction, and a plasma fraction; and (-) returning said cell enriched fraction and said plasma fraction to said donor/patient through said donor tubing by admixing said plasma fraction from said first container through said fifth connection to flow of said cell enriched fraction from said reservoir passing through said second connection.

5. Method as claimed in claim 4 wherein said cell enriched fraction and said plasma fraction being returned to the donor/patient are mixed prior to reintroduction into the donor patient through peristaltic pump action.

6. Machine for leukocyte apheresis comprising: a tubing operable for connection to a donor/patient for the drawing of blood therefrom and subsequent return of leukocyte depleted blood thereto; a centrifugal separating means for separation of blood into various components including at least an erythrocyte enriched fraction, a leukocyte enriched fraction, and a plasma fraction; a reservoir for the erythrocyte enriched fraction which forms an integral portion of the centrifugal separating means; a first pump capable of operating in two opposite directions; a first connection between said first pump and said tubing; a second connection between said first pump and said centrifugal separating means; a first container for said plasma fraction; a third connection from said first container to said centrifugal separating means; a second container for said leukocyte enriched fraction; a fourth connection from said second container to said centrifugal separating means; a fifth connection from said first container to said second connection whereby a junction of said fifth connection and said second connection is formed; and control means operable during return of leukocyte depleted blood to the donor/patient for admixture of said plasma fraction from said first container through said fifth connection to flow of said erythrocyte enriched fraction from said reservoir passing through said second connection.

7. Machine as in claim 6, wherein said control means comprises means for opening and closing alternately and repetitively (i) said second connection between said centrifugal separation means and said junction of said second connection and said fifth connection, and (ii) said fifth connection, respectively.

8. Machine as in claim 6, wherein said control means comprises a second pump for driving a flow of said plasma fraction through said fifth connection, and a means for controlling operation of said second pump.

9. Method for effecting leukocyte apheresis comprising the steps of: (-) connecting a donor/patient to a machine which comprises (*) a tubing operable for connection to a donor/patient for the drawing of blood therefrom and subsequent return of leukocyte depleted blood thereto; (*) a centrifugal separating means for separation of blood into various components including at least a erythrocyte enriched fraction, a leukocyte enriched fraction, and a plasma fraction; (*) a reservoir for the erythrocyte enriched fraction which forms an integral portion of the centrifugal separating means; (*) a first pump capable of operating in two opposite directions; (*) a first connection between said first pump and said tubing; (*) a second connection between said first pump and said separating means; (*) a first container for said plasma fraction; (*) a third connection from said first container to said separating means; (*) a second container for said leukocyte enriched fraction; (*) a fourth connection from said second container to said separating means; (*) a fifth connection from said first container to said second connection whereby a junction of said fifth connection and said second connection is formed; and (*) a control means operable during return of leukocyte depleted blood to the donor/patient for admixture of said plasma fraction from said first container through said fifth connection to flow of said erythrocyte enriched fraction from said reservoir passing through said second connection, (-) withdrawing blood from said donor/patient into said machine; (-) separating said withdrawn blood into at least an erythrocyte enriched fraction, a leukocyte enriched fraction, and a plasma fraction; and (-) returning said erythrocyte enriched fraction and said plasma fraction to said donor/patient through said tubing by admixing said plasma fraction from said first container through said fifth connection to flow of said erythrocyte enriched fraction from said reservoir passing through said second connection.

10. Method as claimed in claim 9, wherein said erythrocyte enriched fraction and said plasma fraction being returned to the donor/patient are mixed prior to reintroduction into the donor/patient through peristaltic pump action.

11. Machine for cytapheresis, comprising:
(-) a donor tubing operable for connection to a donor/patient for the drawing of blood therefrom and subsequent return of said blood after an intermediate density fraction thereof has been removed;
(-) a centrifugal separating means for separation of blood into various components of differing densities including at least a high density fraction, an intermediate density fraction, and a low density fraction;
(-) a reservoir for the high density fraction;
(-) a first pump capable of operating in two opposite directions;
(-) a first connection between said first pump and said donor tubing;
(-) a second connection between said first pump and said separating means;
(-) a first container for said low density fraction;
(-) a third connection from said first container to said separating means;
(-) a second container for said intermediate density fraction;
(-) a fourth connection from said second container to said separating means;
(-) a fifth connection from said first container to said second connection whereby a junction of said fifth connection and said second connection is formed; and (-) control means operable during the return of said low density fraction and said high density fraction to the donor/patient for providing flow of said low density fraction from said first container through said fifth connection and into said second connection so as to admix said low density fraction with said high density fraction flowing from said reservoir through said second connection.

12. Method as claimed in claim 11 wherein said control means alternatively supplies said high density fraction and said low density fraction to a tube connected to the donor/patient.

13. Method as claimed in claim 11 wherein said control means mixes said high density fraction and said low density fraction prior to reintroduction into the donor/patient through peristaltic pump action.

14. Method for effecting platelet apheresis comprising the steps of:
  (-) connecting a donor/patient to a machine which comprises: (*) a donor tubing operable for connection to a donor/patient for the drawing of blood therefrom and subsequent return of platelet depleted blood thereto; (*) a centrifugal separating means for separation of blood into various components, including at least a cell enriched fraction, a platelet enriched fraction, and a plasma fraction; (*) a reservoir for the cell enriched fraction which forms an integral portion of the centrifugal separating means; (*) a first pump capable of operating in two opposite directions; (*) a first connection between said first pump and said donor tubing; (*) a second connection between said first pump and said separating means; (*) a first container for said plasma fraction; (*) a third connection from said first container to said separating means; (*) a second container for said platelet enriched fraction; (*) a fourth connection from said second container to said separating means; (*) a fifth connection from said first container to said second connection whereby a junction of said fifth connection and said second connection is formed; and (*) control means operable during return of platelet depleted blood to the donor/patient for admixture of said plasma fraction from said first container through said fifth connection to flow of said cell enriched fraction from said reservoir passing through said second connection
  (-) withdrawing blood from said donor/patient into said machine;
  (-) separating said withdrawn blood into at least a cell enriched fraction, a platelet enriched fraction, and a plasma fraction; and
  (-) returning said cell enriched fraction and said plasma fraction alternately to said donor/patient through said donor tubing by admixing said plasma fraction from said first container through said fifth connection to flow of said cell enriched fraction from said reservoir passing through said second connection.

15. Method for effecting leukocyte apheresis comprising the steps of: (-) connecting a donor/patient to a machine which comprises (*) a tubing operable for connection to a donor/patient for the drawing of blood therefrom and subsequent return of leukocyte depleted blood thereto; (*) a centrifugal separating means for separation of blood into various components including at least a erythrocyte enriched fraction, a leukocyte enriched fraction, and a plasma fraction; (*) a reservoir for the erythrocyte enriched fraction which forms an integral portion of the centrifugal separating means; (*) a first pump capable of operating in two opposite directions; (*) a first connection between said first pump and said tubing; (*) a second connection between said first pump and said separating means; (*) a first container for said plasma fraction; (*) a third connection from said first container to said separating means; (*) a second container for said leukocyte enriched fraction; (*) a fourth connection from said second container to said separating means; (*) a fifth connection from said first container to said second connection whereby a junction of said fifth connection and said second connection is formed; and (*) a control means operable during return of leukocyte depleted blood to the donor/patient for admixture of said plasma fraction from said first container through said fifth connection to flow of said erythrocyte enriched fraction from said reservoir passing through said second connection, (-) withdrawing blood from said donor/patient into said machine; (-) separating said withdrawn blood into at least an erythrocyte enriched fraction, a leukocyte enriched fraction, and a plasma fraction; and (-) returning said erythrocyte enriched fraction and said plasma fraction alternately to said donor/patient through said tubing by admixing said plasma fraction from said first container through said fifth connection to flow of said erythrocyte enriched fraction from said reservoir passing through said second connection.

16. Method for effecting plasma exchange comprising the steps of: (-) connecting a donor/patient to a machine which comprises (*) a tubing operable for connection to a donor/patient for the drawing of blood therefrom and subsequent return of plasma depleted blood thereto; (*) a centrifugal separating means for separation of blood into various components including at least a cell enriched fraction and a plasma fraction; (*) a reservoir for the cell enriched fraction which forms an integral portion of the centrifugal separating means: (*) a first pump capable of operating in two opposite directions; (*) a first connection between said first pump and said tubing; (*) a second connection between said first pump and said separating means; (*) a first container for said plasma fraction; (*) a third connection from said first container to said separating means; (*) a second container for substitution fluid; (*) a fourth connection from said second container to said second connection whereby a junction of said fourth connection and said second connection is formed; and (*) a control means operable during return of plasma depleted blood to the donor/patient for admixture of said substitution fluid from said second container through said fourth connection to flow of said cell enriched fraction from said reservoir passing through said second connection; (-) withdrawing blood from said donor/patient into said machine; (-) separating said withdrawn blood into at least a cell enriched fraction and a plasma fraction; and (-) returning said cell enriched fraction and said substitution fluid to said donor/patient through said donor tubing by admixing said substitution fluid alternately from said second container through said fourth connection to flow of said cell enriched fraction from said reservoir passing through said second connection.

* * * * *